United States Patent [19]
Davis

[11] Patent Number: 5,388,589
[45] Date of Patent: Feb. 14, 1995

[54] CORE BIOPSY NEEDLE WITH SPACER

[75] Inventor: Richard E. Davis, Grand Rapids, Mich.

[73] Assignee: DLP, Inc., Grand Rapids, Mich.

[21] Appl. No.: 158,040

[22] Filed: Nov. 22, 1993

Related U.S. Application Data

[63] Continuation of Ser. No. 767,274, Sep. 27, 1991, abandoned.

[51] Int. Cl.⁶ ............................................. A61B 10/00
[52] U.S. Cl. ................................. 128/754; 128/749; 604/164; 606/167
[58] Field of Search ................. 128/749–754; 606/167, 170–172, 181, 184, 185, 182; 604/158, 164, 165, 209, 210

[56] References Cited

U.S. PATENT DOCUMENTS

| | | | |
|---|---|---|---|
| 3,477,423 | 11/1969 | Griffith | 128/754 |
| 3,598,108 | 8/1971 | Jamshidi et al. | 128/754 |
| 4,266,555 | 5/1981 | Jamshidi | 128/754 |
| 4,600,014 | 7/1986 | Beraha | 128/754 |
| 4,609,370 | 9/1986 | Morrison | 128/754 |
| 4,655,226 | 4/1987 | Lee | 128/754 |
| 4,702,261 | 10/1987 | Cornell et al. | 128/754 |
| 4,776,346 | 10/1988 | Beraha et al. | 128/754 |
| 4,881,551 | 11/1989 | Taylor | 128/754 |
| 4,957,488 | 9/1990 | Cameron et al. | 604/158 |
| 4,958,625 | 9/1990 | Bates et al. | 128/754 |
| 5,031,634 | 7/1991 | Simon | 128/754 |
| 5,236,334 | 8/1993 | Bennett | 128/754 |
| 5,249,582 | 10/1993 | Taylor | 128/754 |
| 5,316,013 | 5/1994 | Striebel et al. | 128/754 |

FOREIGN PATENT DOCUMENTS 9110399 7/1991 WIPO ................................ 128/749

Primary Examiner—Stephen C. Pellegrino
Assistant Examiner—Glenn K. Dawson
Attorney, Agent, or Firm—Barnes, Kisselle, Raisch, Choate, Whittemore & Hulbert

[57] ABSTRACT

A biopsy assembly with an inner stylet having a needle end with a biopsy retrieval recess on the needle end. At the other end of the stylet is a hub for controlling the needle. A hollow outer needle with a main hub at the proximal end carries the inner needle in a sliding relationship. Releasable latch means are provided on the respective hubs to lock them in a fixed but releasable axial position which makes it possible for a physician to enter the spaced hubs in a cocked biopsy gun.

11 Claims, 3 Drawing Sheets

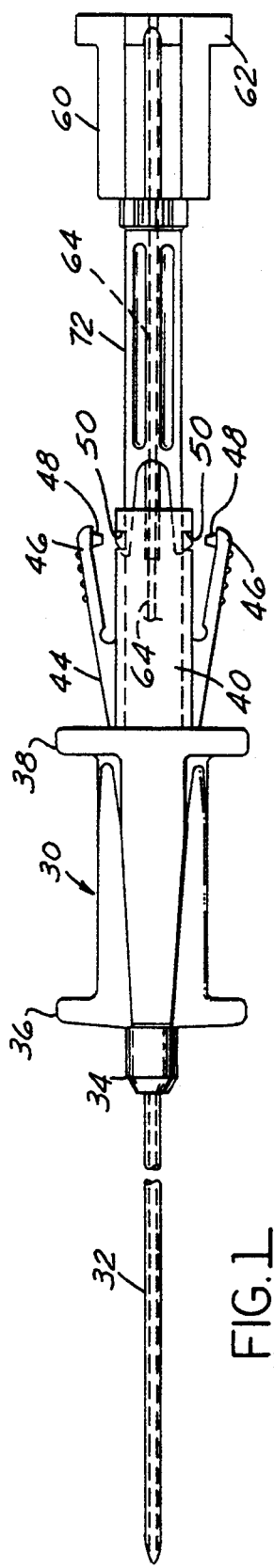
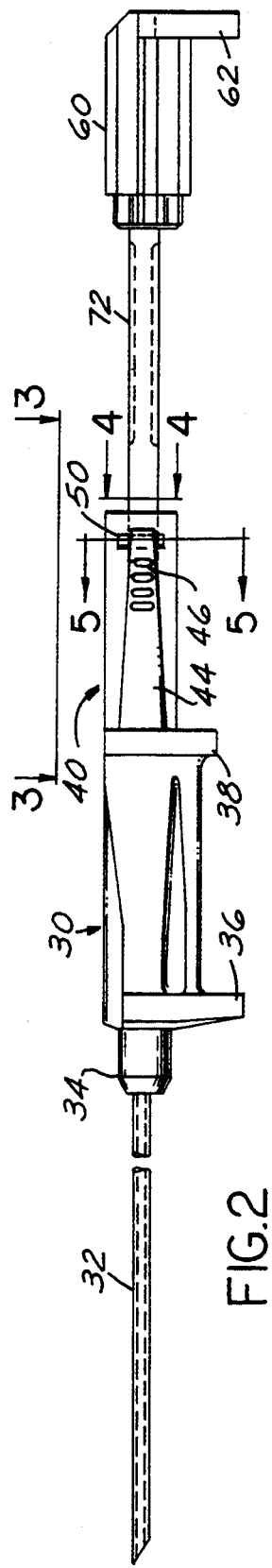
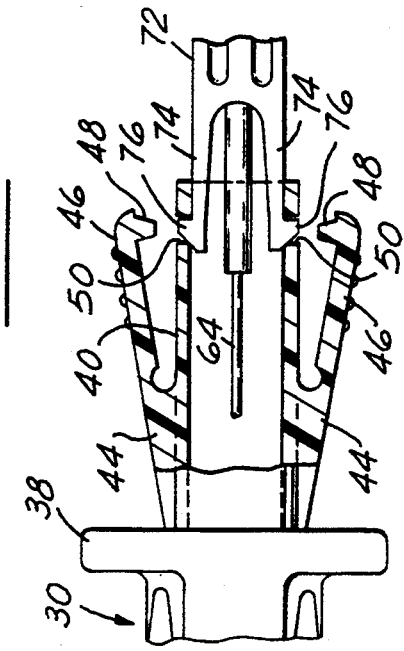
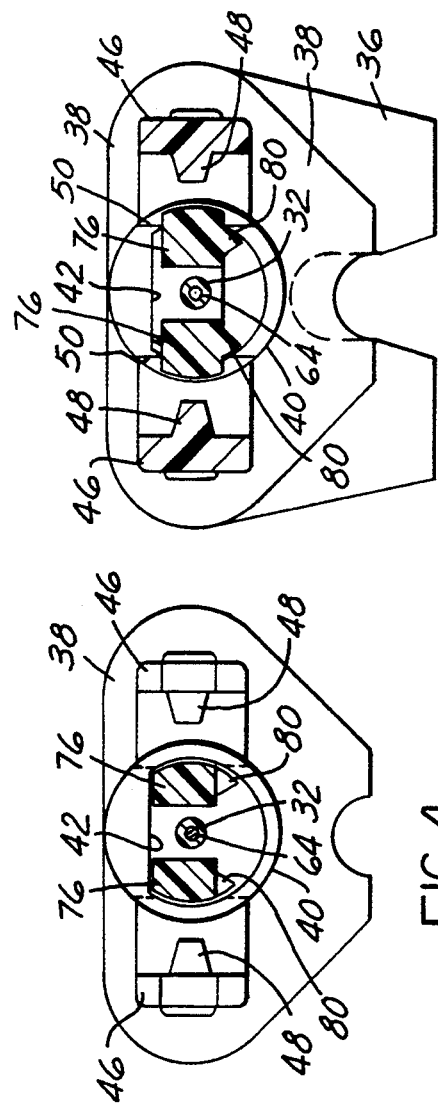
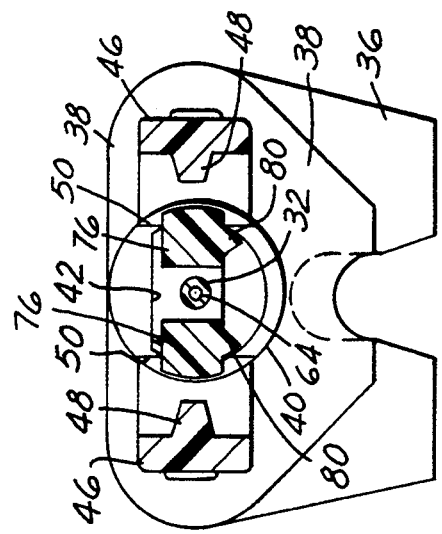

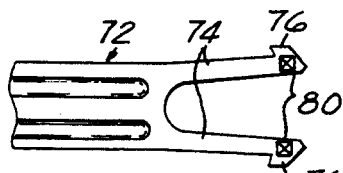
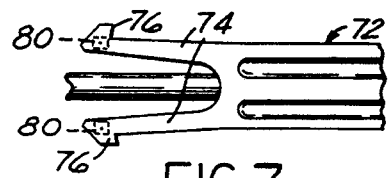
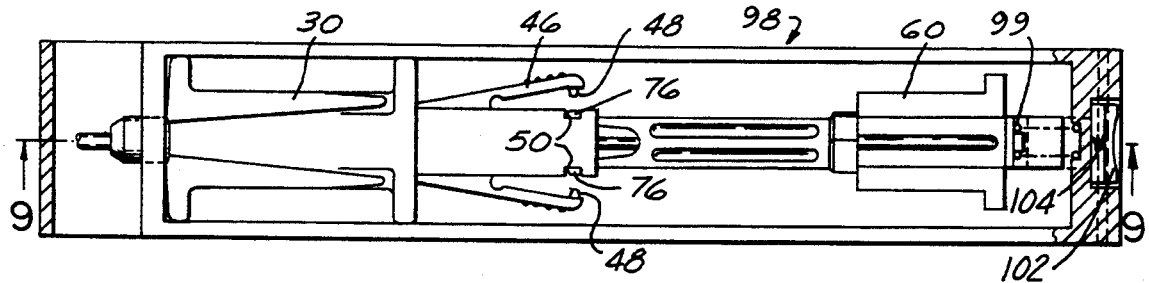
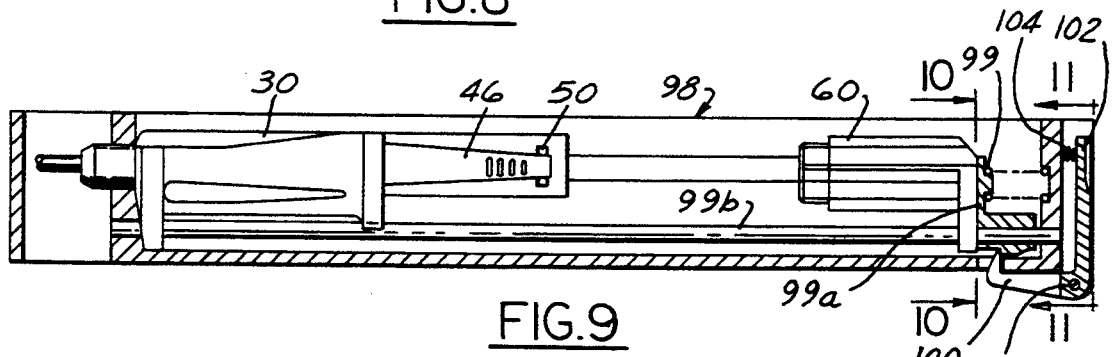
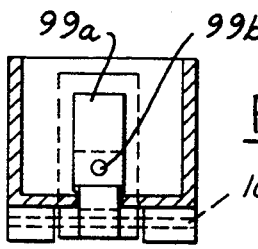
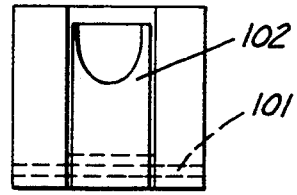
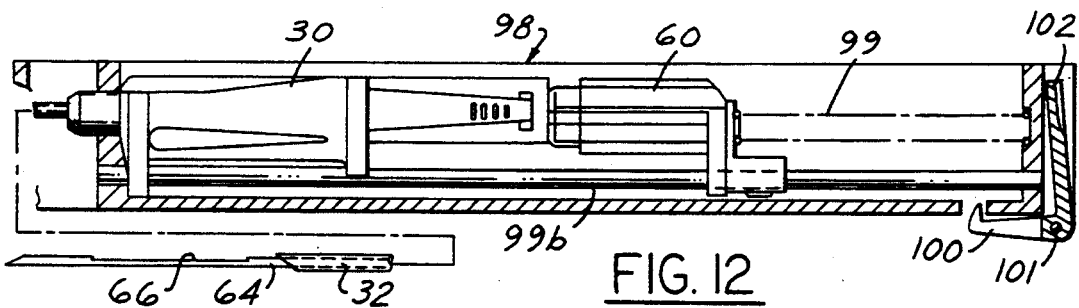
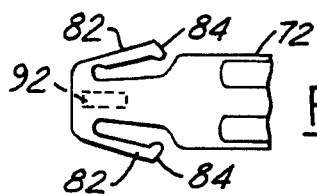
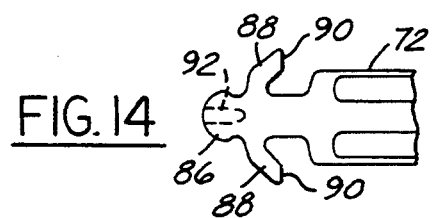

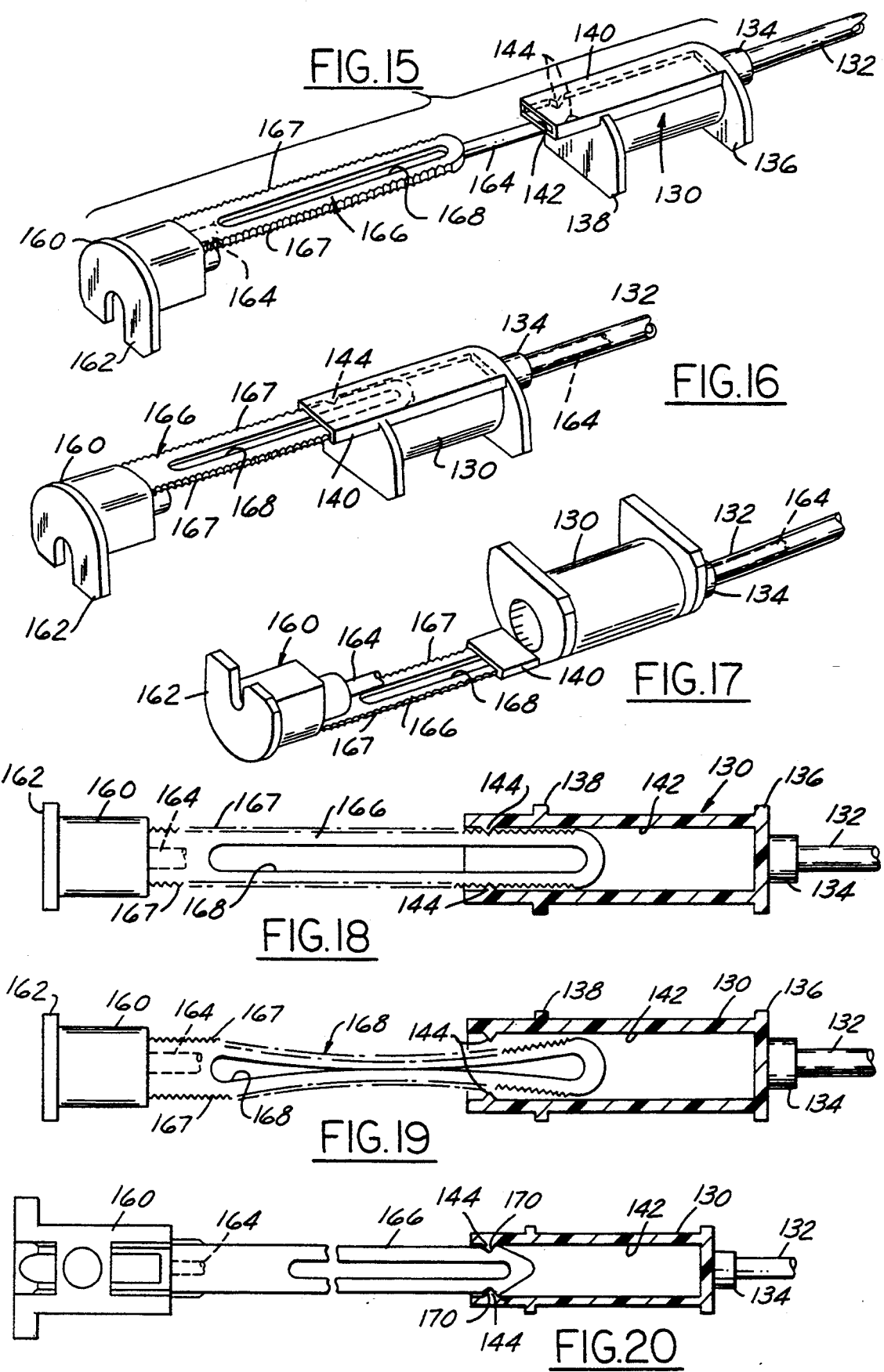

CORE BIOPSY NEEDLE WITH SPACER

This application is a continuation of application Ser. No. 07/767,274, filed Sep. 27, 1991, now abandoned.

FIELD OF INVENTION

The present invention relates to a biopsy needle for tissue sampling using a hollow outer needle and an inner slidable needle.

BACKGROUND AND FEATURES OF THE INVENTION

Tissue sampling devices have been used for some time including an outer needle for enclosing and guiding an inner needle which has, adjacent its outer end, a tissue retrieval means. In one type of biopsy device, when the inner needle is projected out of the outer needle, into the tissue to be sampled, the tissue expands into the recess. Projecting the outer needle over the tissue-filled recess shears the tissue so that a sample remains in the recess. Withdrawing the needles allows retrieval of the sample for biopsy testing. Other biopsy devices also use a hollow outer needle and an inner needle.

In some instances, the introduction of the needles is accomplished manually so that the needles are in the vicinity of the area to be examined. There the needles are mounted in what is called a "biopsy gun" which carries the needles and, when cocked and released, drives the needles in proper sequence into the tissue to receive the sample specimens. One example of a biopsy gun is found in a U.S. Pat. No. 4,699,154, to Radiplast AB, issued Oct. 13, 1987. The use of such a gun enables a single physician to accomplish the biopsy.

The present invention is directed to a biopsy needle assembly which can be mounted in a biopsy gun and which has what may be called a "preset" position, that is, a position in which the point of the inner needle is retracted to the extent that it is adjacent the point of the outer needle. The gun has a sequential release in that the inner needle is first driven forcefully into the tissue about ⅝ of an inch to receive the tissue sample. In the second release the outer needle is projected over the inner needle to shear and capture the specimens.

In order that a physician may successfully operate a biopsy gun, he must first of all cock the gun and, secondly, insert the hub ends of the inner and outer needles into the gun. To facilitate this insertion, the present biopsy needle assembly is constructed to have a pre-loading locator called a "pre-set" position. This enables a physician to set the two hubs of the inner and outer needles prior to initiating the procedure. He can then insert the needles in the area and in the proper direction for the test. Once the needles are placed, the physician can then readily install the hubs into the gun. This is especially important when the physician wants to make more than one biopsy sequentially.

BRIEF DESCRIPTION OF THE INVENTION

Biopsy devices have an inner stylet with a needle end and a specimen recess adjacent the needle end. At the other end of the stylet is a hub for controlling the needle herein referenced as the stylet hub. A hollow outer needle with main hub at the proximal end carries the inner needle in a sliding relation. Releasable latch means are provided on the respective hubs to lock them in a fixed axial position. This fixed position makes it possible for a physician to enter the spaced hubs in a cocked biopsy gun.

BRIEF DESCRIPTION OF THE DRAWINGS

DRAWINGS accompany the disclosure and the various views thereof may be briefly described as:

FIG. 1, a view of the biopsy needle with the stylet hub and main needle hub in extended latched position.

FIG. 2, a view similar to FIG. 1 with the needles turned 90°.

FIG. 3, an enlarged sectional view on line 3—3 of FIG. 2.

FIG. 4, an enlarged sectional view on line 4—4 of FIG. 2.

FIG. 5, an enlarged sectional view on line 5—5 of FIG. 2.

FIGS. 6 and 7, reverse sides of a latch means.

FIG. 8, a view of a biopsy gun with the preset needles in place.

FIG. 9, a sectional view on line 9—9 of FIG. 8.

FIG. 10, a sectional view on line 10—10 of FIG. 9.

FIG. 11, a sectional view on line 11—11 of FIG. 9.

FIG. 12, an intermediate trigger release position of a biopsy gun.

FIG. 13, a view of a latch finger design.

FIG. 14, a view of a modified latch finger design.

FIG. 15, a perspective view of a needle hub and stylet hub separated prior to assembly.

FIG. 16, a perspective view of the hub and stylet with the serrated blade assembled.

FIG. 17, a view of the assembled unit turned 180° from the position shown in FIG. 16.

FIG. 18, a longitudinal section of the assembled parts.

FIG. 19, a view similar to FIG. 18 showing the serrated sides of the blade squeezed to allow disassembly.

FIG. 20, a view of a hub and stylet with a single stop position provided by opposed notches on a stylet blade.

DETAILED DESCRIPTION OF THE INVENTION AND THE MANNER AND PROCESS OF MAKING AND USING IT

In FIGS. 1 and 2, an assembly is shown with a main hub 30 which carries a hollow needle 32 mounted in the distal end in a small boss 34. The hub 30 has two flanges 36 and 38 which are designed to be engaged by a biopsy gun as will be described. A proximal extension 40 is molded with the main hub 30, circular in cross-section of smaller diameter than the main hub and having an out-of-round, acircular recess as a result of a flat section 42 seen in sectional views of FIGS. 4 and 5.

In FIGS. 1 to 5, are shown the extensions 40 with flexible release ears 44 molded integrally with the extension 40 at the root of the extension leaving flexible wings 46 projecting rearwardly. Each of the wings 46 has radially inwardly projection release dogs 48 which, when squeezed, will pass through opposed openings 50 near the proximal end of extension 40.

Again, in FIGS. 1 and 2, a stylet hub 60 is shown with an end flange 62 to engage a biopsy gun. The stylet hub carries the proximal end of a needle 64 which projects into the hollow outer needle 32. In one biopsy procedure, adjacent the sharp, distal end of the stylet is a flat side recess 66 (FIG. 12) which receives a tissue sample as will be described. Other biopsy devices may be used.

On the distal end of stylet hub 60 is a pre-set extension shaft 72 anchored to the hub 60. The distal end of the shaft 72 is formed with a split portion which results in two flexible legs 74 (FIGS. 6 and 7) each having an outwardly extending latch barb 76 which will engage the openings 50 in the extension 40 (FIGS. 1 and 2) when the distal end of the shaft projection 72 is inserted into the extension 40 of the main hub 30.

Projection knobs 80 will engage the flat 42 if the extension is not properly oriented during assembly with respect to the opening in main hub extension 40. In FIGS. 13 and 14, modified designs for split ends of the extension 72 are shown. In FIG. 13, the extension 72 has rearwardly extending legs 82 with blunt ends 84 to engage the holes 50. In FIG. 14, a rounded nose 86 has wings 88 with blunt ends 90 to serve as latches in holes 50. A projection 92 on the bottom surface of nose 86 also serves as an orientation projection as the extension 72 is introduced into the main hub.

From the above description, it will be appreciated that when the needle stylet is inserted into the outer needle 32 and the projection 72 introduced into the rearward extension 40 of the main hub 30, the barbs 76 on the flexible and resilient legs 74 will enter the holes 50 in the tubular extension 40 as the needle stylet is withdrawn. When the needle stylet is moved all the way into the main hub 30, the needle 64 will be advanced as shown in FIG. 12 to expose the recess 66. Withdrawal of the stylet causes the barbs to engage the holes 50. However, squeezing the wings 46 inwardly causes the release dogs 48 to contact the barbs 76 and will release the barbs from the holes 50 so the stylet needle 64 can be withdrawn.

In FIGS. 8 and 9, there is a partially diagrammatic view of a biopsy gun 98 with the hubs 30 and 60 in position as inserted into the gun. The preset position of the hubs, as established by the barbs 76 (FIG. 3), insures that the hubs will position directly into the gun in registry with the projection devices. As viewed in FIGS. 8 and 9, the biopsy gun is loaded and in the cocked position. A spring 99 backs the stylet hub 60 through an L-shaped bracket slide block 99a on a guide rod 99b in the biopsy gun 98. A release trigger 100, mounted on pin 101, is illustrated to be actuated by a lever arm 102 moved against a spring 104. Reference is here made to previously identified U.S. Pat. No. 4,699,154 (1987) which described a biopsy gun and its operation in detail. This patent describes and illustrates a biopsy gun with a main cannula hub and a stylet hub backed by coil springs, each of which can be cocked and released sequentially by a suitable trigger mechanism.

In FIG. 12, the trigger 100 has been tripped and the stylet hub 60 projected forcefully forward to open the recess 66 to the specimen area. A second trigger mechanism will then be actuated to project the outer cannula 32 over the specimen recess 66 to shear the tissue and enclose the specimen. The hubs 30 and 60 can then be removed from the gun and the specimen retrieved by retracting the stylet or withdrawing the hub 30 to expose the specimen recess. Additional specimens may then be obtained. As indicated above, other biopsy needles may be utilized.

The pre-set assembly described in FIGS. 1 to 7 provides safeguards as to orientation of the needle or stylet hub 60 with respect to the main cannula hub. The projections 80, FIGS. 4 and 5, and the flat 42 insure that the proper orientation is obtained. In addition, the longitudinal relationship of the hubs obtained by the barbs 76 entering the opposed openings 50, makes it possible for a physician to readily insert the hub assembly into the biopsy gun. This is especially useful if the physician is operating alone. The locating barbs can be retracted by squeezing the wings 46 so that projections 48 can enter holes 50 and push the barbs inwardly to a release position.

In FIGS. 15 to 19, an embodiment of the invention is illustrated. A main hub 130 carrying an outer hollow needle 132 is mounted in the distal end in a small boss 134. The hub 130 has two flanges 136 and 138 which are designed to be engaged by a biopsy gun as has been described. Formed on the top of the hub 130, as viewed in FIGS. 15 and 16 is a flat housing 140 with a flat recess 142 formed therein extending axially of the hub 130. On side edges of flat passage 142 spaced inwardly of the open end are opposed detent prongs 144.

Also viewed in FIGS. 15 to 19 is a stylet hub 160 with an end flange 162 to engage a biopsy gun. The stylet hub carries the proximal end of a needle 164 which projects into the hollow outer needle 132. The needle 164 may have a flat side recess to receive a tissue sample which is sheared by relative movement of the needles. Mounted on one end of the stylet hub and extending axially away from the proximal end is a flat blade 166 having serrated outside edges 167 and an elongate middle slot 168.

The detent prongs 144 in the flat recess 142 of housing 140 cooperate with the serrations 167. The sides of the blade 166 are flexible so that the blade can slide in and out of the slot 142 and the sides will flex inwardly to accommodate the prongs. However, in the absence of axial pressure, the prongs will maintain the blade in the position set by the physician or technician.

It will be noted that the off-center location of the blade 166 will guide an operator in assembling the main hub 130 and the stylet hub in proper orientation for the interfit of the inner and outer needles.

The assembly of hub 130 and stylet 160 can be set in the desired relationship to be placed in a biopsy gun and after insertion of the needles into a patient, the hub and stylet can be easily inserted into a biopsy gun and the biopsy procedure can be accomplished. The force of the biopsy gun will readily overcome the resistance of the prongs 144 engaged with the serrations 167.

When it is desired to remove the stylet 160 from the hub 130, the sides of the blade 166 can be squeezed together as shown in FIG. 19, and this will release the serrated edges from the detent prongs to the stylet hub and inner needle can be readily separated from the hub 130.

In FIG. 20, an assembly is illustrated wherein the blade 166 is designed to be used in a biopsy gun which has a fixed axially dimensioned recess, when cocked, to receive the biopsy hubs. In this assembly, the blade 166 has opposed notches 170 which cooperate with the detent prongs 144. Thus, when the blade 166 is inserted into the recess 142 of housing 140, the prongs will engage the notches 170 and position the blade in a fixed relationship so that the hubs 130 and 160 are spaced for a biopsy gun having, when cocked, a fixed recess to receive the hubs 130 and 160. The flexible sides of the blade allow resilient release of the prongs when the biopsy gun trigger is released. Removal of the stylet hub is achieved as in FIG. 15.

The embodiments in FIGS. 15 to 19 allow relative positioning of the blade 166 and the hub 130 in varying axial relationships to adapt to biopsy guns which have different recesses for the hubs when cocked.

What is claimed is:

1. In a biopsy needle assembly including an outer cannula having a main hub, and an inner stylet needle having a stylet hub at one end, one of said inner stylet needle and outer cannula having a biopsy recess, the improvement comprising (a) walls surrounding an axial recess in said main hub, said axial recess being acircular in shape having one or more projections extending into the axial recess, (b) an axial projection element on said stylet hub extending toward said main hub and being slidably received in said axial recess of said main hub, said axial projection element on said stylet hub having serrations that receive said one or more projections in said axial recess to locate said axial projection element axially in said recess, and (c) said one or more projections in said axial recess and said serrations on said axial projection element being releasably engagable to space said hubs axially in a predetermined position, said serrations on said axial projection element being movable laterally to be released from said one or more projections in said axial recess.

2. An assembly as defined in claim 1 in which said axial projection has flexible sides, said flexible sides being movable laterally to clear said projections one or more in said recess to allow separation of said main hub and said stylet hub.

3. An assembly as defined in claim 1 in which said projections in said recess are detent prongs formed on opposed sides of said axial recess and which extend into said axial recess recess, and the serrations on said axial projection element are movable laterally to clear said detent prongs.

4. A biopsy needle assembly that comprises:

an outer cannula having a main hub, and an inner stylet needle with a stylet hub at a proximal end and a specimen .recess at a distal end, said cannula and needle being constructed for removable insertion into a biopsy gun having means for engaging said hubs and propelling said needle and then said cannula in sequence from first positions at which said needle and cannula are retracted into said gun and said hubs are at predetermined spacing within said gun relative to each other, through an intermediate position at which said stylet needle extends from said cannula to receive a biopsy specimen in said recess, to second positions at which both said needle and said cannula are extended from said gun and said hubs are at the same said predetermined spacing within said gun relative to each other and the biopsy specimen has been severed and captured in said recess by said cannula, and spacer means of integral construction with said hubs and non-removable from said hubs for releasably locking said hubs to each other and holding said hubs at sa a predetermined spacing at both said first and second positions, such that said cannula and needle assembly is insertable as a unit into said gun to place said hubs at said first positions with said hubs releasably locked at said predetermined spacing, and is removable from said gun as a unit after use with said needle and cannula hubs in sa a second positions and again releasably locked to each other at said predetermined spacing and the biopsy specimen captured by said cannula within said recess in said needle.

5. The assembly set forth in claim 4 wherein said spacer means further includes means for enabling releasable locking of said hubs at said predetermined spacing only at a predetermined rotational orientation of said hubs to each other.

6. The assembly set forth in claim 5 wherein said spacer means comprises an acircular opening at a proximal end of said main hub, means axially projecting from said stylet hub and. slidably disposed within said acircular opening, and spring detent means on said axially projecting means and within said acircular opening for releasably locking said hubs at said predetermined spacing.

7. The assembly set forth in claim 6 wherein said spring detent means comprises first means disposed in fixed position on laterally opposed sides of said acircular opening, and second means facing laterally outwardly from opposed sides of said means axially projecting from said stylet hub for resiliently releasably engaging said first means.

8. The assembly set forth in claim 7 further comprising means for manually resiliently urging said second means laterally inwardly from said first means so as to release locking of said spring detent means.

9. The assembly set forth in claim 8 wherein said means axially projecting from said stylet hub comprises a flat tongue integral with said stylet hub parallel to and radially offset from said styler needle, wherein said first means comprises a pair of detent prongs on respective laterally opposed sides of said acircular opening, and wherein said second means comprises a pair of notches on respective laterally opposed sides of said tongue for releasable engagement with said detent prongs at said predetermined spacing between said hubs.

10. The assembly set forth in claim 9 wherein said second means comprises a plurality of said notches forming a series of serrations on laterally opposed sides of said tongue.

11. The assembly set forth in claim 9 wherein said means for manually resiliently urging said second means includes an elongated slot extending lengthwise of said tongue for permitting resilient motion of side edges of said tongue into said slot.

* * * * *